United States Patent
Fleming et al.

(10) Patent No.: US 11,419,628 B2
(45) Date of Patent: Aug. 23, 2022

(54) TISSUE-REMOVING CATHETER WITH GUIDEWIRE DETECTION SENSOR

(71) Applicant: MEDTRONIC VASCULAR, INC., Santa Rosa, CA (US)

(72) Inventors: Matthew Fleming, Roscommon (IE); Ian Brosnan, Limerick (IE)

(73) Assignee: MEDTRONIC VASCULAR, INC., Santa Rosa, CA (US)

( * ) Notice: Subject to any disclaimer, the term of this patent is extended or adjusted under 35 U.S.C. 154(b) by 366 days.

(21) Appl. No.: 16/565,043

(22) Filed: Sep. 9, 2019

(65) Prior Publication Data

US 2020/0078038 A1    Mar. 12, 2020

Related U.S. Application Data

(60) Provisional application No. 62/729,033, filed on Sep. 10, 2018.

(51) Int. Cl.
*A61B 17/3207* (2006.01)
*A61M 25/01* (2006.01)
*A61M 25/09* (2006.01)

(52) U.S. Cl.
CPC ..... *A61B 17/3207* (2013.01); *A61M 25/0136* (2013.01); *A61M 25/09* (2013.01);
(Continued)

(58) Field of Classification Search
CPC .......... A61B 17/3207; A61B 17/32037; A61B 17/320758; A61B 17/32002;
(Continued)

(56) References Cited

U.S. PATENT DOCUMENTS 2,429,356 A    10/1947 Hicks
5,314,407 A    5/1994 Auth et al.
(Continued)

FOREIGN PATENT DOCUMENTS

WO    WO2006084256 A1    8/2006
WO    WO2013123007 A1    8/2013
(Continued)

OTHER PUBLICATIONS

International Search Report and Written Opinion for PCT Application No. PCT/US2019/050170, dated Nov. 15, 2019, 15 pages, Europe.
(Continued)

*Primary Examiner* — Tuan V Nguyen
(74) *Attorney, Agent, or Firm* — Stinson LLP

(57) ABSTRACT

A tissue-removing catheter for removing tissue in a body lumen includes an elongate body having an axis and proximal and distal end portions spaced apart from one another along the axis. A handle is mounted to the proximal end portion of the elongate body and operable to cause rotation of the elongate body. A tissue-removing element is mounted on the elongate body. The tissue-removing element is configured to remove the tissue as the tissue-removing element is rotated by the elongate body within the body lumen. An inner liner is received within the elongate body and is coupled to the handle at a proximal end portion of the inner liner. The inner liner defines a guidewire lumen. A sensor is arranged with respect to the inner liner and is configured to produce a signal for indicating the presence of a guidewire within the inner liner.

20 Claims, 10 Drawing Sheets

(52) U.S. Cl.
CPC ............... *A61M 2205/3306* (2013.01); *A61M 2205/3317* (2013.01); *A61M 2205/3331* (2013.01)

(58) Field of Classification Search
CPC .... A61B 17/00234; A61M 2025/0166; A61M 2025/50; A61M 2025/3306; A61M 2025/581; A61M 2025/584; A61M 2025/587; A61M 25/09; A61M 25/0127
See application file for complete search history.

(56) References Cited

U.S. PATENT DOCUMENTS

| | | | |
|---|---|---|---|
| 5,569,275 | A | 10/1996 | Kotula et al. |
| 5,779,721 | A | 7/1998 | Nash |
| 6,015,420 | A | 1/2000 | Wulfman et al. |
| 6,113,615 | A | 9/2000 | Wulfman |
| 6,126,667 | A | 10/2000 | Barry et al. |
| 6,145,395 | A | 11/2000 | Kanz et al. |
| 6,270,509 | B1 | 8/2001 | Barry et al. |
| 6,569,177 | B1 | 5/2003 | Dillard et al. |
| 6,632,230 | B2 | 10/2003 | Barry |
| 7,585,300 | B2 | 9/2009 | Cha |
| D766,433 | S | 9/2016 | Blackledge et al. |
| 9,572,492 | B2 | 2/2017 | Simpson et al. |
| 2002/0007190 | A1 | 1/2002 | Wulfman et al. |
| 2010/0280534 | A1 | 11/2010 | Sher |
| 2011/0301626 | A1 | 12/2011 | To et al. |
| 2012/0253372 | A1 | 10/2012 | Ross et al. |
| 2013/0178881 | A1 | 7/2013 | Shturman |
| 2013/0274657 | A1* | 10/2013 | Zirps ................. A61M 25/0147 604/95.01 |
| 2014/0222045 | A1 | 8/2014 | Schneider et al. |
| 2015/0209066 | A1* | 7/2015 | Dahm ............ A61B 17/320758 606/159 |
| 2016/0157886 | A1 | 6/2016 | WasDyke et al. |
| 2018/0133436 | A1 | 5/2018 | Garrison et al. |

FOREIGN PATENT DOCUMENTS

| | | |
|---|---|---|
| WO | WO2016011312 A1 | 1/2016 |
| WO | WO2016073710 | 5/2016 |

OTHER PUBLICATIONS

Boston Scientific Convex Burrs, Rotablator, Rotational Atherectomy System Reference Guide, Apr. 2014, 22 pages, Natick, MA.

* cited by examiner

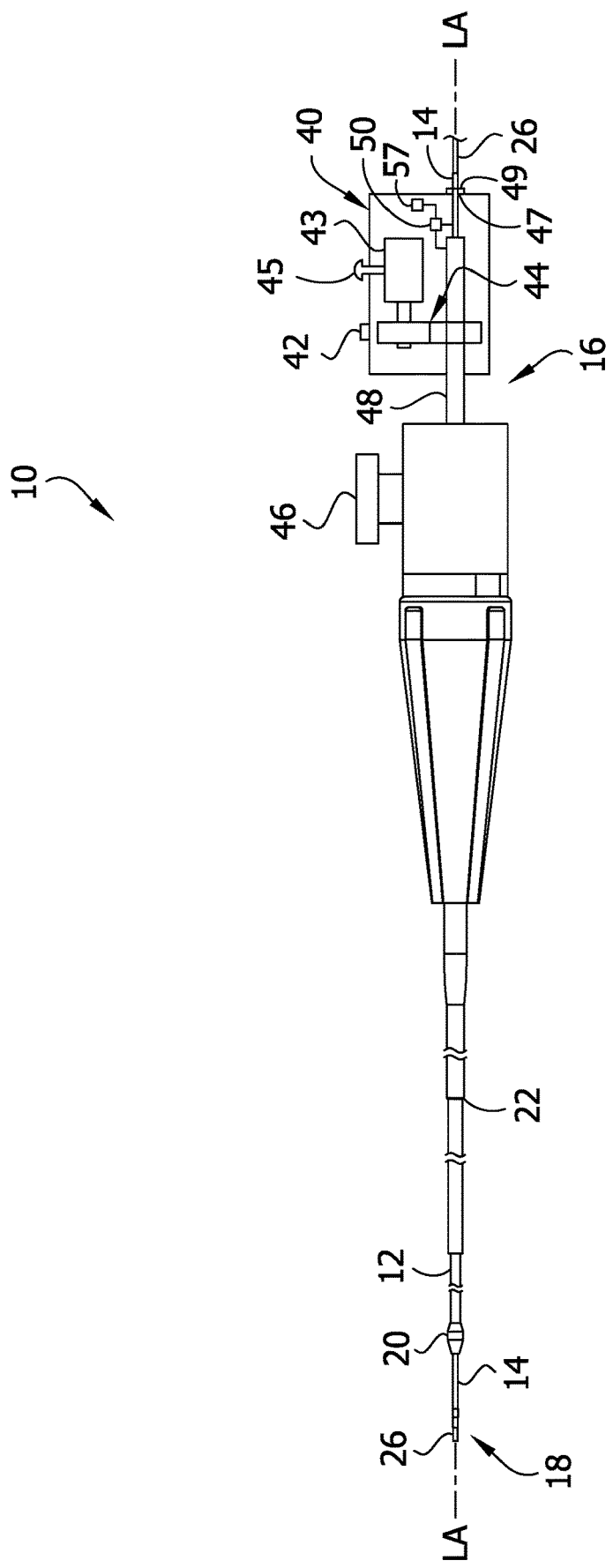

TISSUE-REMOVING CATHETER WITH GUIDEWIRE DETECTION SENSOR

CROSS-REFERENCE TO RELATED APPLICATION

This application claims priority to U.S. Provisional Patent Application Ser. No. 62/729,033, filed Sep. 10, 2018, which is hereby incorporated by reference in its entirety.

FIELD

The present disclosure generally relates to a tissue-removing catheter, and more particular, to a tissue-removing catheter having a guidewire detection sensor.

SUMMARY

In one aspect, a tissue-removing catheter for removing tissue in a body lumen generally comprises an elongate body having an axis and proximal and distal end portions spaced apart from one another along the axis. The elongate body is sized and shaped to be received in the body lumen. A handle is mounted to the proximal end portion of the elongate body and is operable to cause rotation of the elongate body. A tissue-removing element is mounted on the distal end portion of the elongate body. The tissue-removing element is configured to remove the tissue as the tissue-removing element is rotated by the elongate body within the body lumen. An inner liner is received within the elongate body and is coupled to the handle at a proximal end portion of the inner liner. The inner liner defines a guidewire lumen. A sensor is arranged with respect to the inner liner and is configured to produce a signal for indicating the presence of a guidewire within the inner liner.

In another aspect, a tissue-removing catheter for removing tissue in a body lumen generally comprises an elongate body having an axis and proximal and distal end portions spaced apart from one another along the axis. The elongate body is sized and shaped to be received in the body lumen. A tissue-removing element is mounted on the distal end portion of the elongate body. The tissue-removing element is configured to remove the tissue as the tissue-removing element is rotated by the elongate body within the body lumen. An inner liner is received within the elongate body. The inner liner defines a guidewire lumen. A sensor is arranged with respect to the inner liner and is configured to produce a signal for indicating the presence of a guidewire within the inner liner.

In yet another aspect, a method of removing tissue in a body lumen generally comprises advancing a tissue-removing catheter over a guidewire in the body lumen to position a distal end of the catheter adjacent the tissue and a proximal end portion of the catheter outside of the body lumen. The catheter comprises an elongate body, a tissue removing element mounted on a distal end portion of the elongate body, and an inner liner disposed within the elongate body. The inner liner defines a guidewire lumen in which the guidewire is disposed during the advancement of the catheter. The method further comprises detecting whether the guidewire is present within the inner liner.

BACKGROUND

Tissue-removing catheters are used to remove unwanted tissue in body lumens. As an example, atherectomy catheters are used to remove material from a blood vessel to open the blood vessel and improve blood flow through the vessel. This process can be used to prepare lesions within a patient's coronary artery to facilitate percutaneous coronary angioplasty (PTCA) or stent delivery in patients with severely calcified coronary artery lesions. Atherectomy catheters typically employ a rotating element which is used to abrade or otherwise break up the unwanted tissue.

BRIEF DESCRIPTION OF THE DRAWINGS

FIG. 1 is an elevation of a catheter of the present disclosure;

Corresponding reference characters indicate corresponding parts throughout the drawings.

DETAILED DESCRIPTION

Figure 1A:
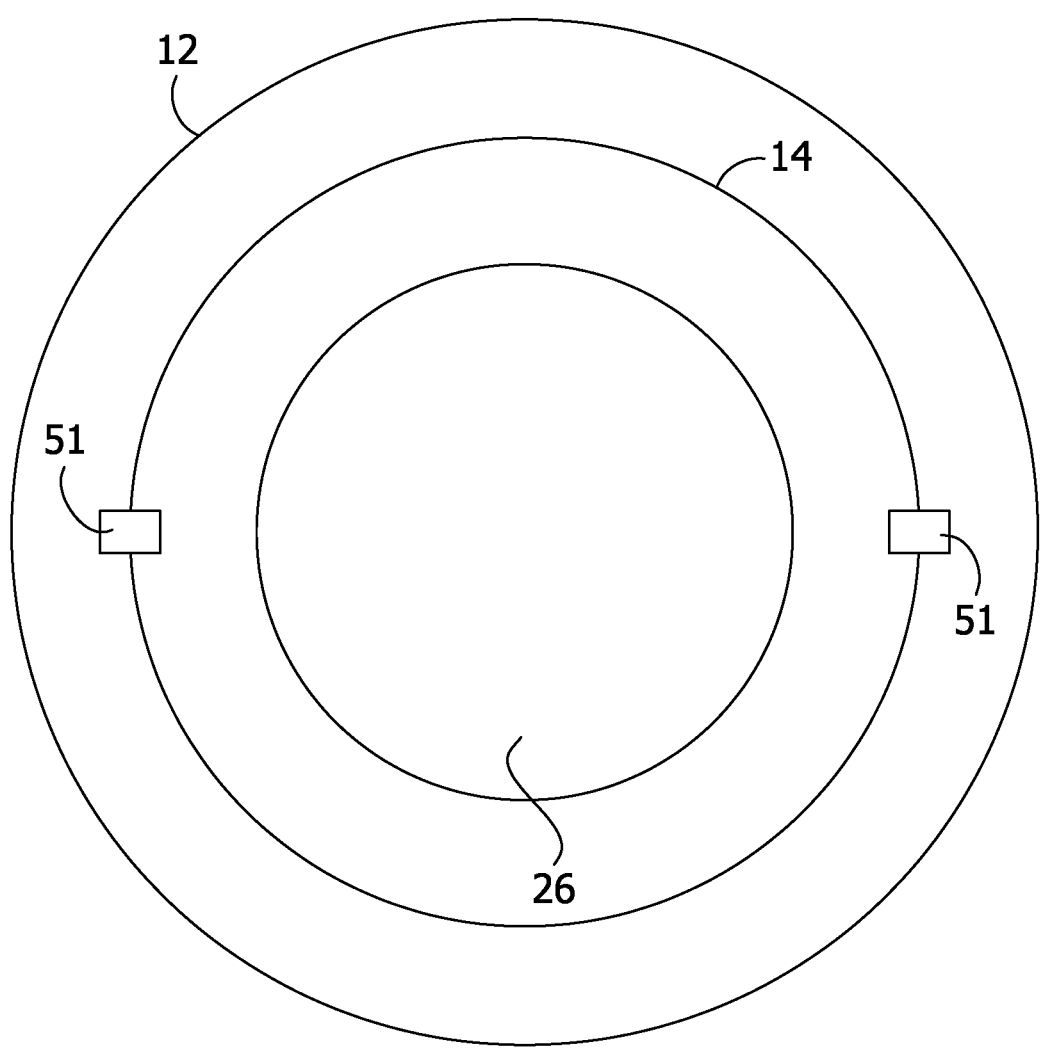
FIG. 1A is a schematic illustration of a guidewire detection circuit of the catheter.

Referring to the drawings, and in particular FIG. 1, a rotational tissue-removing catheter for removing tissue in a body lumen is generally indicated at reference number 10. The illustrated catheter 10 is a rotational atherectomy device suitable for removing (e.g., abrading, cutting, excising, ablating, etc.) occlusive tissue (e.g., embolic tissue, plaque tissue, atheroma, thrombolytic tissue, stenotic tissue, hyperplastic tissue, neoplastic tissue, etc.) from a vessel wall (e.g., coronary arterial wall, etc.). The catheter 10 may be used to facilitate percutaneous coronary angioplasty (PTCA) or the subsequent delivery of a stent. Features of the disclosed embodiments may also be suitable for treating chronic total occlusion (CTO) of blood vessels, and stenoses of other body lumens and other hyperplastic and neoplastic conditions in other body lumens, such as the ureter, the biliary duct, respiratory passages, the pancreatic duct, the lymphatic duct, and the like. Neoplastic cell growth will often occur as a result of a tumor surrounding and intruding into a body lumen. Removal of such material can thus be beneficial to maintain patency of the body lumen.

The catheter 10 is sized for being received in a blood vessel of a subject. Thus, the catheter 10 may have a maximum size of 3, 4, 5, 6, 7, 8, 9, 10, or 12 French (1, 1.3, 1.7, 2, 2.3, 2.7, 3, 3.3, or 4 mm) and may have a working length of 20, 30, 40, 60, 80, 100, 120, 150, 180 or 210 cm depending of the body lumen. While the remaining discussion is directed toward a catheter for removing tissue in blood vessels, it will be appreciated that the teachings of the present disclosure also apply to other types of tissue-removing catheters, including, but not limited to, catheters for penetrating and/or removing tissue from a variety of occlusive, stenotic, or hyperplastic material in a variety of body lumens.

Figure 2:
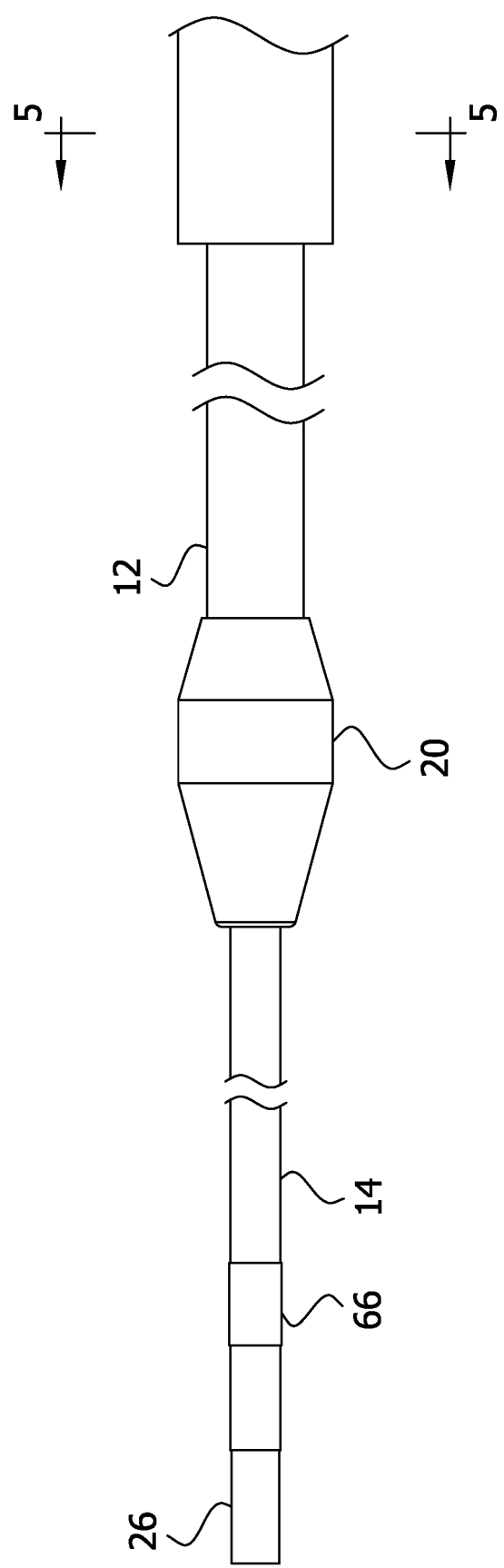
FIG. 2 is an enlarged elevation of a distal end portion of the catheter.
Figure 5:
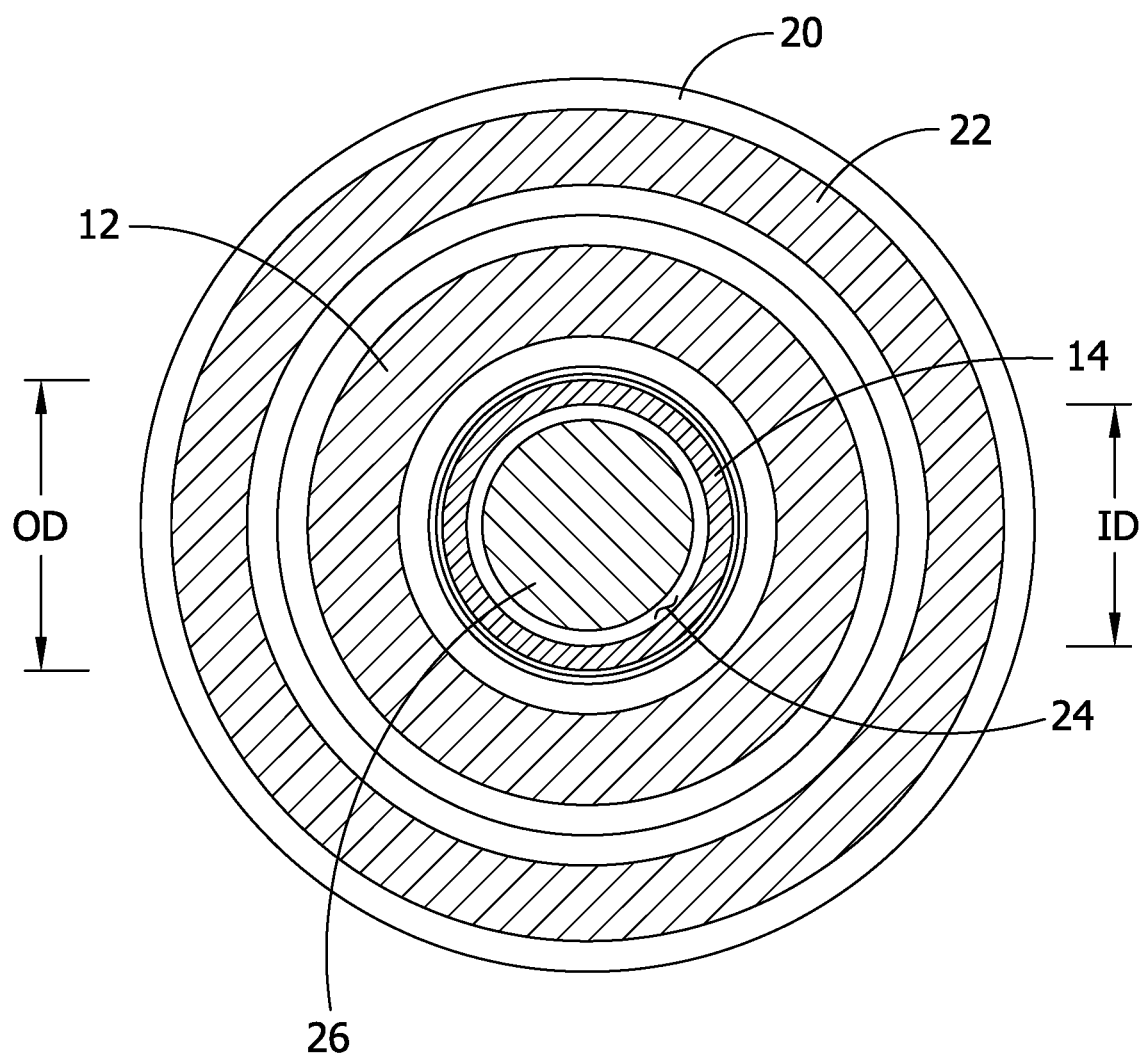
FIG. 5 is a cross section taken through line 5-5 in FIG. 2.
Figure 6:
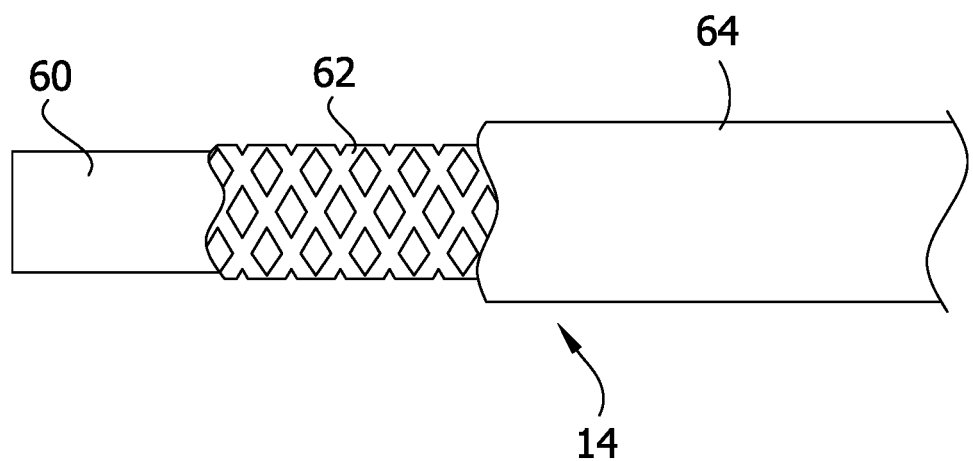
FIG. 6 is a fragmentary elevation of an isolation liner of the catheter with portions broken away to show internal details.

Referring to FIGS. 1 and 2, the catheter 10 comprises an elongate outer layer 12 (broadly, an elongate body) disposed around an elongate inner liner 14. The outer layer 12 and inner liner 14 extend along a longitudinal axis LA of the catheter from a proximal end portion 16 to a distal end portion 18 of the catheter. A tissue-removing element 20 is disposed on a distal end of the outer layer 12 and is configured for rotation to remove tissue from a body lumen as will be explained in greater detail below. A sheath 22 (FIG. 1) is disposed around the outer layer 12. The outer layer 12 and the inner liner 14 are both configured to translate relative to the sheath 22. The outer layer 12 and inner liner 14 are also configured to translate relative to each other. The catheter 10 is sized and shaped for insertion into a body lumen of a subject. The sheath 22 isolates the body lumen from at least a portion of the outer layer 12 and inner liner 14. The inner liner 14 defines a guidewire lumen 24 (FIG. 5) for slidably receiving a guidewire 26 therein so that the catheter 10 can be advanced through the body lumen by traveling along the guidewire. The guidewire can be a standard 0.014 inch outer diameter, 300 cm length guidewire. In certain embodiments, the inner liner 14 may have a lubricious inner surface for sliding over the guidewire 26 (e.g., a lubricious surface may be provided by a lubricious polymer layer or a lubricious coating). In the illustrated embodiment, the guidewire lumen 24 extends from the proximal end portion 16 through the distal end portion 18 of the catheter 10 such that the guidewire 26 is extendable along an entire working length of the catheter 10. In one embodiment, the overall working length of the catheter 10 may be between about 135 cm (53 inches) and about 142 cm (56 inches). In use, the guidewire 26 may extend about 40 mm (1.6 inches) past a distal end of the inner liner 14.

The catheter 10 further comprises a handle 40 secured at the proximal end portion 16 of the catheter. The handle 40 supports an actuator 42 (e.g., a lever, a button, a dial, a switch, or other device) configured for selectively actuating a motor 43 disposed in the handle to drive rotation of the outer layer 12, and tissue-removing element 20 mounted at the distal end of the outer layer. The motor 43 is configured to rotate the outer layer 12 and tissue removing element 20 at speeds of greater than about 80,000 RPM. The motor 43 is coupled to the outer layer 12 by a gear assembly 44 and drive 48 supported by the handle 40. A slide or advancer 45 is positioned on the handle 40 and is operatively coupled to the outer layer 12 for movement of the outer layer relative to the handle to advance and retract the outer layer and tissue-removing element 20. The handle 40 defines a slot (not shown) which limits the movement of the slide 45 relative to the handle. Thus, the length of the slot determines the amount of relative movement between the outer layer 12 and the handle 40. In one embodiment, the slot has a length of about 70 mm (2.8 inches). A perfusion port 46 may be disposed at the proximal end 16 of the catheter 10. The port 46 communicates with a space between the sheath 22 and the outer layer 12 for delivering fluid (e.g., saline) to cool the rotating outer layer during use. A proximal port 47 allows for passage of the guidewire 26 and inner liner 14 through the proximal end of the handle 40. A guidewire lock 49 (FIG. 1) may be provided on the handle 40 to lock the guidewire 26 in place relative to the handle. In one embodiment, the guidewire lock 49 is automatically engaged when the actuator 42 is actuated to rotate the outer layer 12.

It is understood that other suitable actuators, including but not limited to touchscreen actuators, wireless control actuators, automated actuators directed by a controller, etc., may be suitable to selectively actuate the motor in other embodiments. In some embodiments, a power supply may come from a battery (not shown) contained within the handle 40. The battery can provide the current source for the guidewire detection circuit. In other embodiments, the power supply may come from an external source.

Figure 3:
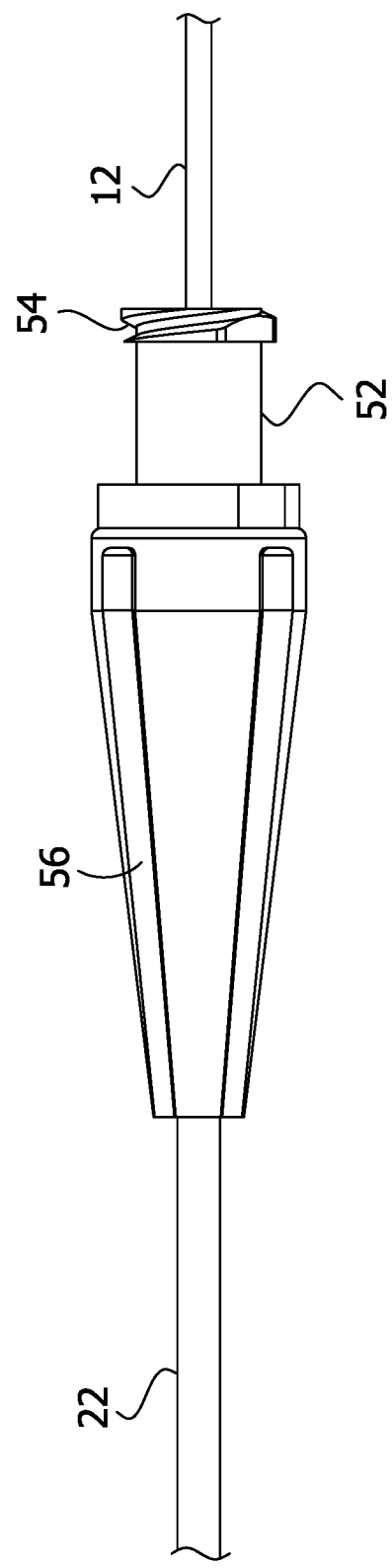
FIG. 3 is an enlarged elevation of a proximal end portion of the catheter.
Figure 4:
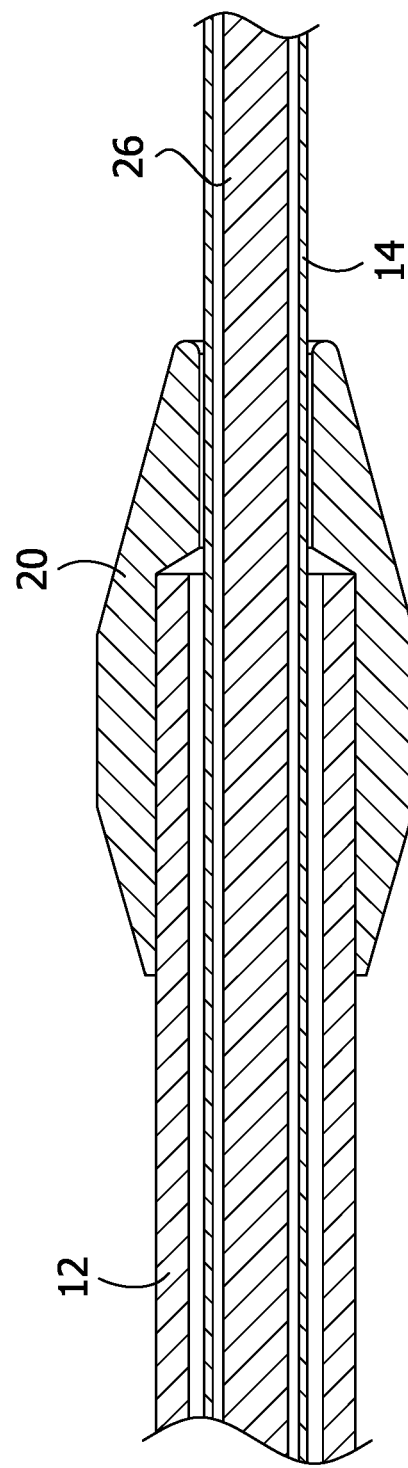
FIG. 4 is an enlarged fragmentary longitudinal cross section of the distal end portion of the catheter in FIG. 2.

Referring to FIGS. 1 and 3, the outer sheath 22 comprises a tubular sleeve configured to isolate and protect a subject's arterial tissue within a body lumen from the rotating outer layer 12. The sheath 22 is fixed to the handle 40 at a proximal end of the sheath and does not rotate. A hub 52 mounted on the proximal end of the sheath 22 attaches the sheath to the handle 40. The hub 52 includes a locking feature 54 (e.g., threaded luer lock) for engaging the handle 40 to attach the sheath 22 to the handle. The sheath 22 provides a partial enclosure for the outer layer 12 and inner liner 14 to move within the sheath. The inner diameter of the sheath 22 is sized to provide clearance for the outer layer 12. The space between the sheath 22 and the outer layer 12 allows for the outer layer to rotate within the sheath and provides an area for saline perfusion between the sheath and outer layer. The outer diameter of the sheath 22 is sized to provide clearance with an inner diameter of a guide catheter (not shown) for delivering the catheter 10 to the desired location in the body lumen. A strain relief 56 is provided at the proximal end of the sheath 22 to alleviate tension applied to the proximal end of the sheath 22 as the sheath is bent during use of the catheter 10. In one embodiment, the sheath 22 has an inner diameter of about 0.050 inches (1.27 mm), an outer diameter of about 0.055 inches (1.4 mm), and a length of about 1500 mm (59 inches). The sheath 22 can have other dimensions without departing from the scope of the disclosure. In one embodiment, the outer sheath 22 is made from Polytetrafluorethylene (PTFE). Alternatively, the outer sheath 22 may comprise a multi-layer construction. For example, the outer sheath 22 may comprises an inner layer of perfluoroalkox (PFA), a middle braided wire layer, and an outer layer of Pebax.

Referring to FIGS. 1, 2, 4, and 5, the outer layer 12 may comprise a tubular stainless steel coil configured to transfer rotation and torque from the motor 43 to the tissue-removing element 20. Configuring the outer layer 12 as a coiled structure provides the outer layer with a flexibility that facilitates delivery of the catheter 10 through the body lumen. Also, the coil configuration allows for the rotation and torque of the outer layer 12 to be applied to the tissue-removing element 20 when the catheter 10 is traversed across a curved path. The stiffness of the outer layer 12 also impacts the ease at which the coil is traversed through the body lumen as well as the coil's ability to effectively transfer torque to the tissue-removing element 20. In one embodiment, the outer layer 12 is relatively stiff such that axial compression and extension of the coil is minimized during movement of the catheter 10 through a body lumen. The coil configuration of the outer layer 12 is also configured to expand its inner diameter when the coil is rotated so that the outer layer remains spaced from the inner liner 14 during operation of the catheter 10. In one embodiment, the outer layer 12 has an inner diameter of about 0.023 inches (0.6 mm) and an outer diameter of about 0.035 inches (0.9 mm). The outer layer 12 may have a single layer construction. For example, the outer layer may comprise a 7 filar (i.e., wire) coil with a lay angle of about 30 degrees. Alternatively, the outer layer 12 could be configured from multiple layers without departing from the scope of the disclosure. For example, the outer layer 12 may comprise a base coil layer and a jacket (e.g., Tecothane™) disposed over the base layer. In one embodiment, the outer layer comprises a 15 filar coil with a lay angle of about 45 degrees. The Tecothane™ jacket may be disposed over the coil. Alternatively, the outer layer 12 may comprise a dual coil layer configuration which also includes an additional jacket layer over the two coil layers. For example, the outer layer may comprise an inner coil layer comprising a 15 filar coil with a lay angle of about 45 degrees, and an outer coil layer comprising a 19 filar coil with a lay angle of about 10 degrees. Outer layer having other configurations are also envisioned.

Referring to FIGS. 1, 2, and 4-6, the inner liner 14 comprises a multiple layer tubular body configured to isolate the guidewire 26 from the outer layer 12 and tissue-removing element 20. The inner liner 14 is extendable through the handle 40 from a position proximal of the handle to a position distal of the handle. In one embodiment, the inner liner 14 is coupled to the handle 40 but is not fixedly attached to the handle 40 to allow translation of the inner liner relative to the handle. In this embodiment, rotation of the inner liner 14 is not prevented. However, the clearance between the inner liner 14 and the outer layer 12 prevents any rotation of the inner liner caused by the rotation of the outer layer. In this embodiment, both the inner liner 14 and outer layer 12 are permitted to translate relative to the handle 40. Allowing this co-translation of the inner liner 14 and outer layer 12 minimizes compression and extension of the coiled outer layer 14 when force is applied to the outer layer to move the outer layer within the body lumen. In another embodiment, the inner liner 14 may be fixedly attached to the handle 40 to prevent relative movement between the inner liner and the handle. Thus, in this embodiment, the inner liner 14 remains stationary and is prevented from translating relative to the handle 40. Additionally, all rotation of the inner liner 14 is prevented. In this embodiment, the outer layer 12 translates over the stationary inner liner 14.

The inner liner 14 has an inner diameter that is sized to pass the guidewire 26. The inner liner 14 protects the guide wire from being damaged by the rotation of the outer layer 12 by isolating the guidewire from the rotatable outer layer. The inner liner 14 also extends past the tissue-removing element 20 to protect the guidewire 26 from the rotating tissue-removing element. Thus, the inner liner 14 is configured to prevent any contact between the guidewire 26 and the rotating components of the catheter 10. Therefore, any metal-to-metal engagement is eliminated by the inner liner 14. This isolation of the outer layer 12 and tissue-removing element 20 from the guidewire 26 also ensures that the rotation of the outer layer and tissue-removing element is not transferred or transmitted to the guidewire. As a result, a standard guidewire 26 can be used with the catheter 10 because the guidewire does not have to be configured to withstand the torsional effects of the rotating components. Additionally, by extending through the tissue-removing element 20 and past the distal end of the tissue-removing element, the inner liner 14 stabilizes the tissue-removing element by providing a centering axis for rotation of the tissue-removing element about the inner liner.

In the illustrated embodiment, the inner liner 14 comprises an inner PTFE layer 60 an intermediate braided layer 62 comprised of stainless steel, and an outer layer 64 of polyimide. The PTFE inner layer 60 provides the inner liner 14 with a lubricous interior which aids in the passing of the guidewire 26 though the inner liner. The braided stainless steel intermediate layer 62 provides rigidity and strength to the inner liner 14 so that the liner can withstand the torsional forces exerted on the inner liner by the outer layer 12. In one embodiment, the intermediate layer 62 is formed from 304 stainless steel. The outer polyimide layer 64 provides wear resistance as well as having a lubricous quality which reduces friction between the inner liner 14 and the outer layer 12. Additionally, a lubricious film, such as silicone, can be added to the inner liner 14 to reduce friction between the inner liner and the outer layer 12. In one embodiment, the inner liner 14 has an inner diameter ID of about 0.016 inches (0.4 mm), an outer diameter OD of about 0.019 inches (0.5 mm), and a length of about 59 inches (1500 mm). The inner diameter ID of the inner liner 14 provides clearance for the standard 0.014 inch guidewire 26. The outer diameter OD of the inner liner 14 provides clearance for the outer layer 12 and tissue-removing element 20. Having a space between the inner liner 14 and the outer layer 12 reduces friction between the two components as well as allows for saline perfusion between the components.

In the illustrated embodiment, a marker band 66 is provided on an exterior surface of the distal end of the inner liner 14. The marker band 66 configures the tip of the inner liner 14 to be fluoroscopically visible which allow a physician to verify the position of the liner during a medical procedure. In this embodiment, the distal end of the inner liner 14 may be laser cut to provide a low profile tip. In one embodiment, the marker band 66 comprises a strip of platinum iridium.

Figure 7:
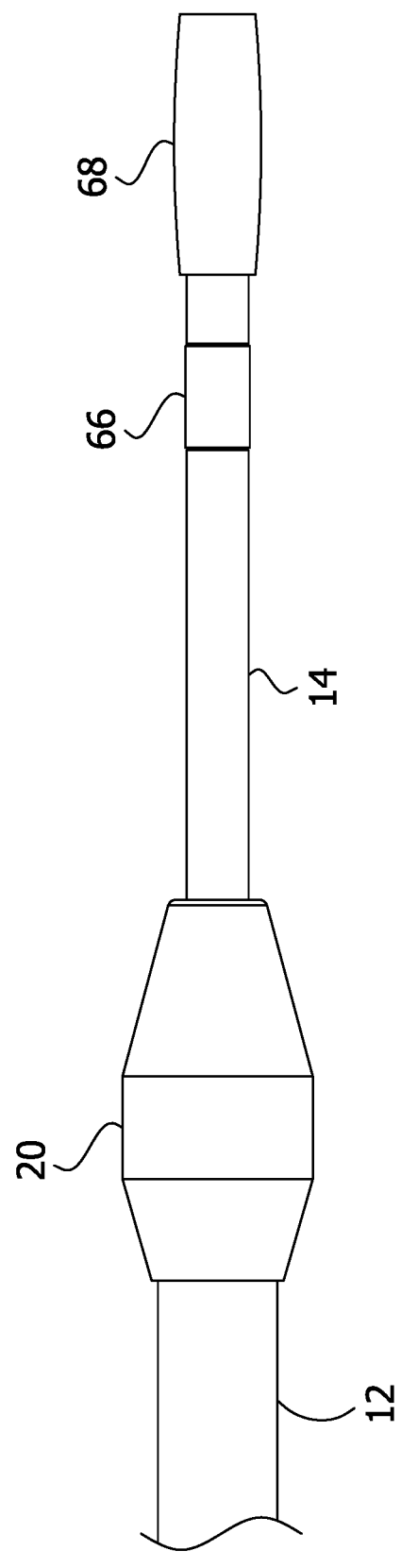
FIG. 7 is an enlarged elevation of a distal end portion of the catheter showing an atraumatic tip on an inner liner.
Figure 8:
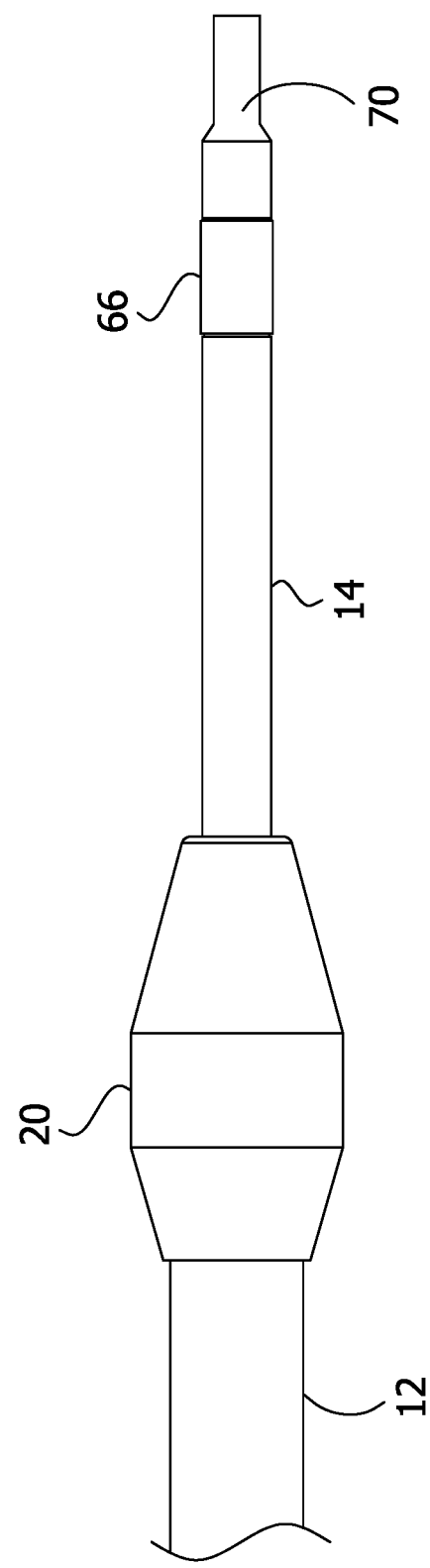
FIG. 8 is an enlarged elevation of a distal end portion of the catheter showing a tapered tip on an inner liner.

It is further envisioned that the distal end of the inner liner 14 can have other constructions without departing from the scope of the disclosure. For example, an atraumatic tip 68 may be attached to the distal end of the inner liner 14 (FIG. 7). The atraumatic tip 68 provides a soft, low profile distal end to facilitate delivery of the inner liner 14 through the body lumen without causing trauma. The atraumatic tip 68 may have a maximum outer diameter of about 0.02 inches (0.6 mm). Other sizes of the atraumatic tip are also envisioned. In another embodiment, a tapered tip 70 may be attached to the distal end of the inner liner 14 (FIG. 8). The tapered tip 70 may be formed from a layer of material configured to protect the distal end of the inner liner 14.

Referring to FIGS. 1 and 1A, a controller 50 may be provided in the handle 40. The controller 50 may be programmed to detect a signal indicating the position of the guidewire 26 relative to the inner liner 14. For example, the controller 50 may detect a signal indicating whether the guidewire 26 is present generally at a distal end portion of the inner liner 14. The controller 50 may be configured to produce an alarm signal (e.g., audible sound, visual indication, etc.) and/or prevent or halt rotation of the outer layer 12 when no guidewire is detected at the distal end portion of the inner liner 14. Alternatively, if the guidewire 26 is detected at the distal end portion of the inner liner 14, the controller 50 may permit, in the form of continuing or initiating, rotation of the outer layer 12. The guidewire detection may be accomplished by locating one or more sensors 51 at the distal end portion of the inner liner 14. The controller 50 is in electrical communication with the sensors 51 such that the sensors can send a signal to the controller indicating the presence of the guidewire 26.

Ideally, the inner liner 14 is disposed around a portion of the guidewire 26 such that the guidewire extends distally from the inner liner. This ensures that the entire length of the catheter 10 is supported by the guidewire 26 so that the catheter can be properly and safely navigated through the body. Also, with the guidewire 26 extending through the distal end of the inner liner 14, the tissue removing element 20 will be properly supported for rotation by the guidewire. In this event, if the guidewire 26 is correctly positioned, the one or more sensors 51 will detect the presence of the guidewire at the distal end portion of the inner liner 14. However, if the inner liner 14 or guidewire 26 have been moved relative to each other such that the distal end portion of the inner liner extends past a distal end of the guidewire, then no portion of the guidewire will be at the distal end portion of the inner liner and the sensors 51 will not detect the presence of a guidewire. Because the controller 50 is in electrical communication with the one or more sensors 51 and can receive signals from the sensors, the controller 50 may then signal an alarm component 57 and/or prevent or halt rotation of the outer layer 12 if no guidewire is detected.

Referring to FIGS. 1 and 1A, the sensors 51 are located generally at the distal end portion of the inner liner 14 and are suitably attached to the inner liner. In one embodiment, the sensors 51 are attached to an exposed surface of inner liner 14. In another embodiment, the sensors 51 are at least partially embedded in the inner liner. The sensors 51 may be any type of sensor configured to detect the presence of the guidewire 26. For example, the sensors 51 may be optical sensors, magnetic sensors, pressure sensors, or any other type of sensor for detecting the presence of the guidewire 26. In the embodiment where the sensors 51 are optical sensors, a first sensor (emitter) 51 may emit a beam of light toward a second sensor (detector) 51 for detecting the light emitted from the first sensor. In this embodiment, the controller 50 will interpret a lack of signal from the detector 51 as an indication that the guidewire 26 is present. This would be a result of the guidewire 26 blocking the light emitted from the emitter 51 from reaching the detector 51. Conversely, if a signal is detected at the detector 51, the controller will interpret this condition as an indication that the guidewire 26 is not present. Alternatively, the controller 50 may interpret a lack of signal from the detector 51 as an indication that the guidewire 26 is not present, and the presence of a signal as an indication that the guidewire is present. For instance, the guidewire 26 may direct the emitted light from the emitter to the detector so that a received signal from the detector is an indication that the guidewire is present.

If the one or more sensors 51 are magnetic sensors, the sensors may be located at the marker band 66 on the inner liner 14. The magnetic sensors 51 detect a magnetic field around the sensor and use this information as an indication of the presence of the guidewire 26. Because the guidewire 26 is metallic, the guidewire will affect the magnetic field around the sensors 51 when the guidewire is present at the distal end portion of the inner liner 14. However, if the guidewire 26 is not present at the distal end portion of the inner liner 14, then the magnetic field around the sensor 51 will not be affected by the guidewire. The controller 50 will interpret the affected magnet field signal from the sensors 51 as an indication that the guidewire 26 is present at the distal end portion of the inner liner 14.

In the embodiment where the one or more sensors 51 are pressure sensors, the sensors are located to detect pressure changes caused by contact from the guidewire 26. As the guidewire 26 is moved within the inner liner 14, it is typical for the guidewire to at least partially contact the inner wall of the inner liner. By locating pressure sensors 51 at the distal end portion of the inner liner 14, the engagement of the guidewire 26 with the inner liner can be detected. Therefore, the controller 50 will interpret a positive pressure signal from the sensors 51 as an indication that the guidewire 26 is present at the distal end portion of the inner liner 14, and a lack of a positive pressure signal as an indication that the guidewire is not present at the distal end portion of the inner liner.

Additionally or alternatively, the one or more sensors 51 could be located in the tissue removing element 20. In this embodiment, the sensors 51 may be magnetic sensors. However, the sensors could be other types of sensors without departing from the scope of the disclosure.

The one or more sensors 51 may be electrically connected to the controller 50 by any suitable manner. In one embodiment, the sensors 51 are electrically connected to the intermediate braided layer 62 of the inner liner 14 at a distal end portion of the inner liner, and the controller 50 is electrically connected to the intermediate braided layer 62 at a proximal end portion of the inner liner. The metallic construction of the intermediate braided layer 62 conducts the electrical signal between the sensors 51 and the controller 50. Alternatively, a fourth layer (not shown) could be provided in the inner liner 14 for conducting the electrical signals between the sensors 51 and the controller 50. In one embodiment, the fourth layer comprises electro-ink microsensors configured to transmit an electrical signal. The sensors 51 would be electrically connected to the fourth layer at a distal end portion of the fourth layer, and the controller 50 would be electrically connected to a proximal end portion of the fourth layer. Electro-ink microsensors may also be incorporated into other layers of the inner liner 14 for electrically connecting the one or more sensors 51 to the controller 50. In embodiments where the sensors 51 are located in the tissue-removing element 20, the sensors can be electrically connected to the controller through the outer layer 12. The metallic construction of the outer layer 12 and drive 48 is configured to conduct the electrical signal between the sensors 51 and the controller 50. Alternatively, an additional layer (not shown) can be used in the catheter 10 for electrically connecting the one or more sensors 51 to the controller 50.

Figure 9:
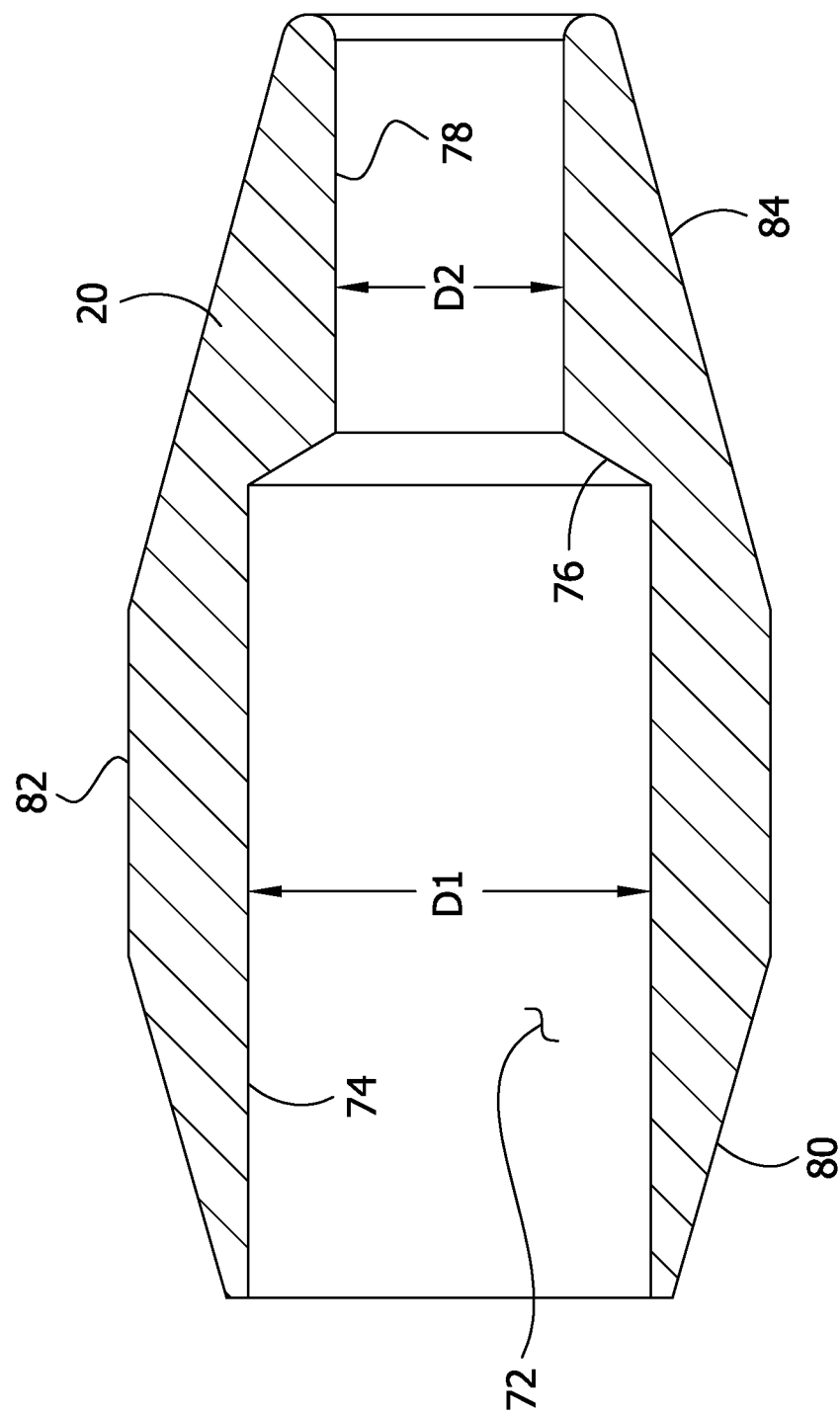
FIG. 9 is an enlarged longitudinal cross section of a tissue-removing element of the catheter.

Referring to FIGS. 1, 2, and 9, the tissue-removing element 20 extends along the longitudinal axis LA from a proximal end adjacent the distal end portion of the outer layer 12 to an opposite distal end. The tissue-removing element 20 is operatively connected to the motor 43 for being rotated by the motor. When the catheter 10 is inserted into the body lumen and the motor 43 is rotating the tissue-removing element 20, the tissue-removing element is configured to remove occlusive tissue in the body lumen to separate the tissue from the wall of the body lumen. Any suitable tissue-removing element for removing tissue in the body lumen as it is rotated may be used in one or more embodiments. In one embodiment, the tissue-removing element 20 comprises an abrasive burr configured to abrade tissue in the body lumen when the motor 43 rotates the abrasive burr. The abrasive burr 20 may have an abrasive outer surface formed, for example, by a diamond grit coating, surface etching, or the like. In one embodiment, the tissue-removing element comprises a stainless steel spheroid body with an exterior surface including 5 µm of exposed diamond crystals. The tissue-removing element 20 may also be radiopaque to allow the tissue-removing element to be visible under fluoroscopy. In other embodiments, the tissue-removing element can comprise one or more cutting elements having smooth or serrated cutting edges, a macerator, a thrombectomy wire, etc.

A cavity 72 extends longitudinally through the tissue-removing element 20 such that the tissue-removing element defines openings at its proximal and distal ends. The cavity 72 receives a portion of the outer layer 12 for mounting the tissue-removing element 20 to the outer layer. The cavity 72 includes a first diameter portion 74 extending from the proximal end of the tissue-removing element 20, a tapered diameter portion 76 extending from the first diameter portion toward the distal end of the tissue-removing element, and a second diameter portion 78 extending from the tapered diameter portion to the distal end of the tissue-removing element. The diameters of the first and second diameter portions 74, 78 are constant along their lengths. In the illustrated embodiment, a diameter D1 of the first diameter portion 74 is larger than a diameter D2 of the second diameter portion 78. In one embodiment, the diameter D1 of the first diameter portion 74 is about 0.035 inches (0.9 mm), and the diameter D2 of the second diameter portion 78 is about 0.022 inches (0.56 mm). The tapered diameter portion 76 provides a transition between the first and second diameter portions 74, 78. The outer layer 12 is received in the first diameter portion 74 and a distal end of the outer layer abuts the tapered diameter portion 76. The tissue-removing element 20 can be fixedly attached to the distal end of the outer layer 12 by any suitable means. In one embodiment an adhesive bonds the tissue-removing element 20 to the outer layer 12. The inner liner 14 extends through the outer layer 12 and the second diameter portion 78 of the tissue-removing element 20. The second diameter portion 78 is sized to pass the inner liner 14 with a small clearance. The inner diameter D2 provides clearance between the tissue-removing element 20 and inner liner 14 to reduce friction between the components and allow a space for saline perfusion. Accordingly, the tissue-removing element 20 is shaped and arranged to extend around at least a portion of the outer layer 12 and inner liner 14 and thus provides a relatively compact assembly for abrading tissue at the distal end portion of the catheter 10.

The exterior surface of the tissue-removing element 20 includes a proximal segment 80, a middle segment 82, and a distal segment 84. A diameter of the proximal segment 80 increases from the proximal end of the tissue-removing element 20 to the middle segment 82. The middle segment has a constant diameter and extends from the proximal segment 80 to the distal segment 84. The diameter of the distal segment 84 tapers from the middle segment 82 to the distal end of the tissue-removing element 20. The tapered distal segment 84 provides the tissue-removing element 20 with a general wedge shape configuration for wedging apart constricted tissue passages as it simultaneously opens the passage by removing tissue using the abrasive action of the tissue-removing element. The distal end of the tissue-removing element 20 is also rounded to provide the tissue-removing element with a blunt distal end.

Referring to FIGS. 1 and 2, to remove tissue in the body lumen of a subject, a practitioner inserts the guidewire 26 into the body lumen of the subject, to a location distal of the tissue that is to be removed. Subsequently, the practitioner inserts the proximal end portion of the guidewire 26 through the guidewire lumen 24 of the inner liner 14 and through the handle 40 so that the guidewire extends through the proximal port 47 in the handle. The inner liner 14 may also extend through the handle 40 and out the proximal port 47. With the catheter 10 loaded onto the guidewire 26, the practitioner advances the catheter along the guidewire until the tissue-removing element 20 is positioned proximal and adjacent the tissue. When the tissue-removing element 20 is positioned proximal and adjacent the tissue, the practitioner actuates the motor 43 using the actuator 42 to rotate the outer layer 12 and the tissue-removing element mounted on the outer layer. The tissue-removing element 20 abrades (or otherwise removes) the tissue in the body lumen as it rotates. While the tissue-removing element 20 is rotating, the practitioner may selectively move the outer layer 12 and inner liner 14 distally along the guidewire 26 to abrade the tissue and, for example, increase the size of the passage through the body lumen. The practitioner may also move the outer layer 12 and inner liner 14 proximally along the guidewire 26, and may repetitively move the components in distal and proximal directions to obtain a back-and-forth motion of the tissue-removing element 20 across the tissue. If at any point the guidewire 26 becomes positioned away from the distal end portion of the inner liner 14, the guidewire detection circuity may automatically deactivate the motor 43 to cease or halt rotation of the outer layer 12 and tissue-removing element 20. Repositioning the guidewire 26 in the distal end portion of the inner liner 14 may automatically reactivate the motor 43 to cause rotation of the outer layer 12 and tissue-removing element 20 to restart. During the abrading process, the inner liner 14 isolates the guidewire 26 from the rotating outer layer 12 and tissue-removing element 20 to protect the guidewire from being damaged by the rotating components. As such, the inner liner 14 is configured to withstand the torsional and frictional effects of the rotating outer layer 12 and tissue-removing element 20 without transferring those effects to the guidewire 26. When the practitioner is finished using the catheter 10, the catheter can be withdrawn from the body lumen and unloaded from the guidewire 26 by sliding the catheter proximally along the guidewire. The guidewire 26 used for the abrading process may remain in the body lumen for use in a subsequent procedure.

When introducing elements of the present invention or the one or more embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above apparatuses, systems, and methods without departing from the scope of the invention, it is intended that all matter contained in the above description and shown in the accompanying drawings shall be interpreted as illustrative and not in a limiting sense.

What is claimed is:

1. A tissue-removing catheter for removing tissue in a body lumen, the tissue-removing catheter comprising:
   an elongate body having an axis and proximal and distal end portions spaced apart from one another along the axis, the elongate body being sized and shaped to be received in the body lumen;
   a handle mounted to the proximal end portion of the elongate body and operable to cause rotation of the elongate body;
   a tissue-removing element mounted on the distal end portion of the elongate body, the tissue-removing element being configured to remove the tissue as the tissue-removing element is rotated by the elongate body within the body lumen;
   an inner liner received within the elongate body and coupled to the handle at a proximal end portion of the inner liner, the inner liner defining a guidewire lumen; and
   a sensor arranged with respect to the inner liner and configured to produce a signal for indicating the presence of a guidewire within the inner liner.

2. A tissue-removing catheter as set forth in claim 1, wherein the sensor is located at a distal end portion of the inner liner.

3. A tissue-removing catheter as set forth in claim 2, wherein the sensor comprises one of an optical, magnetic, and pressure sensor.

4. A tissue-removing catheter as set forth in claim 1, wherein the sensor comprises a first sensor, the catheter further comprising a second sensor arranged with respect to the inner liner and configured to indicate the presence of a guidewire within the inner liner.

5. A tissue-removing catheter as set forth in claim 4, wherein the first sensor comprises an emitter for emitting light and the second sensor comprises a detector for detecting the light emitted by the emitter, the detection of light by the detector providing an indication of whether a guidewire is present within the inner liner.

6. A tissue-removing catheter as set forth in claim 1, wherein the sensor is attached to the inner liner.

7. A tissue-removing catheter as set forth in claim 6, wherein the sensor is at least partially embedded in the inner liner.

8. A tissue-removing catheter as set forth in claim 6, further comprising a marker band on the inner liner, wherein the sensor is attached to the marker band.

9. A tissue-removing catheter as set forth in claim 1, wherein the sensor is attached to the tissue-removing element and electrically connected to the elongate body.

10. A tissue-removing catheter as set forth in claim 1, wherein the inner liner comprises electrically conductive material, the sensor being connected to the electrically conductive material.

11. A tissue-removing catheter as set forth in claim 10, wherein the electrically conductive material comprises a metal layer of the inner liner.

12. A tissue-removing catheter as set forth in claim 10, wherein the electrically conductive material comprises electro-ink.

13. A tissue-removing catheter as set forth in claim 1, further comprising a controller operatively connected to the sensor for receiving the signal from the sensor indicating whether a guidewire is present within the inner liner.

14. A tissue-removing catheter as set forth in claim 13, wherein the controller is disposed in the handle.

15. A tissue-removing catheter as set forth in claim 13, further comprising a motor in the handle and operatively engaging the elongate body for driving rotation of the elongate body and tissue-removing element mounted on the elongate body, the controller permitting the motor to rotate the elongate body when the signal from the sensor indicates that a guidewire is present within the inner liner and preventing the motor from rotating the elongate body when the signal from the sensor indicates that no guidewire is present within the inner liner.

16. A tissue-removing catheter as set forth in claim 15, wherein the handle includes a guidewire lock configured to lock the guidewire in place relative to the handle, the controller automatically engaging the guidewire lock when the motor is activated for driving rotation of the elongate body and tissue-removing element.

17. A tissue-removing catheter for removing tissue in a body lumen, the tissue-removing catheter comprising:
an elongate body having an axis and proximal and distal end portions spaced apart from one another along the axis, the elongate body being sized and shaped to be received in the body lumen;
a tissue-removing element mounted on the distal end portion of the elongate body, the tissue-removing element being configured to remove the tissue as the tissue-removing element is rotated by the elongate body within the body lumen;
an inner liner received within the elongate body, the inner liner defining a guidewire lumen; and
a sensor arranged with respect to the inner liner and configured to produce a signal for indicating the presence of a guidewire within the inner liner.

18. A tissue-removing catheter as set forth in claim 17, wherein the sensor comprises one of an optical, magnetic, and pressure sensor.

19. A method of removing tissue in a body lumen, the method comprising:
advancing a tissue-removing catheter over a guidewire in the body lumen to position a distal end of the catheter adjacent the tissue and a proximal end portion of the catheter outside of the body lumen, the catheter comprising an elongate body, a tissue removing element mounted on a distal end portion of the elongate body, and an inner liner disposed within the elongate body, the inner liner defining a guidewire lumen in which the guidewire is disposed during the advancement of the catheter; and
detecting a position of the guidewire within the inner liner by a sensor arranged with respect to the inner liner.

20. A method of claim 19, further comprising rotating the elongate body and tissue-removing element of the catheter to remove the tissue when the guidewire is detected at a distal end portion of the inner liner, and one of preventing or ceasing rotation of the elongate body and tissue-removing element when the guidewire is not detected at the distal end portion of the inner liner.

* * * * *